(12) United States Patent
Hayashida et al.

(10) Patent No.: US 9,624,535 B2
(45) Date of Patent: Apr. 18, 2017

(54) METHOD FOR DETECTING METHYLATED CYTOSINE BY USING BISULFITE REACTION

(71) Applicant: Wako Pure Chemical Industries, Ltd., Osaka-shi, Osaka (JP)

(72) Inventors: Yukinobu Hayashida, Amagasaki (JP); Naoyuki Yamamoto, Amagasaki (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 284 days.

(21) Appl. No.: 14/364,545

(22) PCT Filed: Dec. 10, 2012

(86) PCT No.: PCT/JP2012/081936
§ 371 (c)(1),
(2) Date: Jun. 11, 2014

(87) PCT Pub. No.: WO2013/089063
PCT Pub. Date: Jun. 20, 2013

(65) Prior Publication Data
US 2015/0176069 A1    Jun. 25, 2015

(30) Foreign Application Priority Data
Dec. 14, 2011    (JP) .................. 2011-272868

(51) Int. Cl.
*C12Q 1/68*    (2006.01)

(52) U.S. Cl.
CPC ......... *C12Q 1/6858* (2013.01); *C12Q 1/6806* (2013.01)

(58) Field of Classification Search
None
See application file for complete search history.

(56) References Cited

FOREIGN PATENT DOCUMENTS

WO    WO 2005/021563 A2    3/2005

OTHER PUBLICATIONS

Miura et al., *Experimental Medicine*, 28(15): 2407-2414 (Sep. 10, 2010).
Raizis et al., *Anal. Biochem.*, 226(1): 161-166 (1995).
Qiagen, EpiTect® Bisulfite Handbook., Sample & Assay Technologies, pp. 1-48 (Sep. 2009).
Wako Bio Window, EpiSight Bisulfite Conversion Kit / EpiSight BisulTaq DNA Polymerase, No. 114, pp. 2-3 (Jan. 2012).
Japanese Patent Office, International Search Report in International Patent Application No. PCT/JP2012/081936 (Feb. 5, 2013).

*Primary Examiner* — David Thomas
(74) *Attorney, Agent, or Firm* — Leydig, Voit & Mayer, Ltd.

(57) ABSTRACT

The invention provides a method for converting non-methylated cytosine in a single-stranded DNA into uracil by a bisulfite reaction with a high conversion efficiency from non-methylated cytosine into uracil. The invention also provides a method for amplifying the single-stranded DNA in which non-methylated cytosine has been converted into uracil, as well as a method for detecting methylated cytosine in the single-stranded DNA.

17 Claims, 3 Drawing Sheets

```
         10          20          30          40          50          60
GGTTGGGGTC TCTCCAGGTG ACAGTAGCCA CCGCCAGGCC CGCGCCTCCT CCCCCGGCGG
         70          80          90         100         110         120
TGATTGGCAG GCGGCCTGCG CCCCGGCTCC CAGGCGACCG ACGCCCCGCG GGGCAGGCGA
        130         140         150         160         170         180
GTAGGAGGGG GCGCCGGCTA TATATACCAC TGCTCCGGAG GGCTGGGCGC GCGGGGACTA
        190         200         210         220         230         240
TCCCGCCACC GTTGCGTCCC TATTTGCTCT CGCTACTTAG GTCTGTGCGC AGCACTCACC
        250         260         270         280         290         300
GAACTCACGG CCCGCAGCTC GAACTCACGC ACGGCCCGCG GGCCGGGATG GCGAAACGCG
        310         320         330         340         350         360
GGCCGACCAC AGGGACGCTG CTGCCCAGGG TCCTGCTGGC CCTGGTGGTG GCCCTGGCGG
        370         380         390         400         410         420
ACCGAGGGAC CGCCGCACCC AACGGCACGC GGCACGCAGA ATTGGGGCAC GGCTGGGACG
        430         440         450         460         470         480
GCTTGGTGGC CCGCTCGCTG GCACGCCTGC CGGTGGCCGC GCAGCCCCCG CAGGCGGCGG
        490         500         510         520         530
TCCGCAGCGG CGCAGGGGAC TACCTGCTGG GCCTCAAAAG G
```

METHOD FOR DETECTING METHYLATED CYTOSINE BY USING BISULFITE REACTION

CROSS-REFERENCE TO RELATED APPLICATIONS

This patent application is the U.S. national phase of International Patent Application No. PCT/JP2012/081936, filed Dec. 10, 2012, which claims the benefit of Japanese Patent Application No. 2011/272868, filed on Dec. 14, 2011, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 1,870 bytes ASCII (Text) file named "716980 Replacement-SequenceListing.txt," created Sep. 29, 2014.

TECHNICAL FIELD

The present invention relates to a method for converting non-methylated cytosine in single-stranded DNA into uracil by a novel bisulfite reaction, a method for amplifying single-stranded DNA in which non-methylated cytosine has been converted into uracil, and a method for detecting methylated cytosine in the single-stranded DNA.

BACKGROUND ART

It has been known that methylation of genomic DNA in a living organism is caused to suppress expression of mRNA. Further, it has been reported that the difference of methylation pattern on a genome relates to genesis, differentiation, and disease such as cancer, and therefore the analysis of methylation of genomic DNA has an important role in finding out the cause and prevention of disease, development of medicinal products, research on the regenerative medicine, and so on.

On the other hand, as the method for determining methylated cytosine in DNA nucleotide sequence, a method for comparing the fragments by methylation-sensitive restriction enzyme, a bisulfite method, a methylation-specific PCR method, and a method which utilizes a high performance liquid chromatography (HPLC), etc have been known. Among them, the bisulfite method has become popular as a common method because the bisulfite method is low cost and applicable to high throughput, and is also effective for sequencing and screening.

SUMMARY OF THE INVENTION

Problem to be Solved by the Invention

Since conversion rate from non-methylated cytosine into uracil is not high in the conventional bisulfite method, the bisulfite method had problems of low accuracy etc. in detection of methylated cytosine. Therefore, until now, development of a bisulfite method having high conversion efficiency from non-methylated cytosine into uracil has been desired.

It is an object of the present invention to provide a method for converting non-methylated cytosine in a single-stranded DNA into uracil by a novel bisulfite reaction with higher conversion efficiency from non-methylated cytosine into uracil as compared with the conventional bisulfite method, a method for amplifying the single-stranded DNA in which non-methylated cytosine has been converted into uracil, and a method for detecting methylated cytosine in the single-stranded DNA.

Means for Solving the Problem

In view of the above-described situation, the present inventors have investigated extensively to develop a bisulfite method having high accuracy. As a result, the present inventors have found that non-methylated cytosine can be converted into uracil efficiently by making at least one of compounds selected from the compounds shown by the following general formula [1] to [8] coexist at the time of bisulfite reaction, and thus the present invention has been achieved; a compound shown by the following general formula [1]

[1]

wherein $R_1$ to $R_6$ represent each independently a hydrogen atom or an alkyl group having 1 to 6 carbon atoms; n represents an integer of 1 to 3;

a compound shown by the following general formula [2]

[2]

wherein Y represents a carbon atom, an oxygen atom or a nitrogen atom; $R_7$ to $R_{12}$ represent each independently a hydrogen atom or an alkyl group having 1 to 6 carbon atoms; k represents an integer of 0 to 2, and when Y is an oxygen atom, k represents 0, when Y is a nitrogen atom, k represents 1, and when Y is a carbon atom, k represents 2;

a compound shown by the following general formula [3]

[3]

wherein $R_{13}$ to $R_{15}$ represent each independently a hydrogen atom or an alkyl group having 1 to 6 carbon atoms;

a compound shown by the following general formula [4]

wherein $R_{17}$ and $R_{19}$ represent each independently a hydrogen atom, an amino group or an alkyl group having 1 to 6 carbon atoms; $R_{16}$, $R_{18}$ and $R_{20}$ represent each independently a hydrogen atom, an amino group, an alkyl group having 1 to 6 carbon atoms or a dialkylamino group having 2 to 6 carbon atoms; and $R_{16}$ and $R_{17}$ may form a benzene ring together with a carbon atom adjacent to $R_{16}$ and a carbon atom adjacent to $R_{17}$;

a compound shown by the following general formula [5]

wherein $R_{21}$ and $R_{22}$ represent each independently an alkyl group having 1 to 6 carbon atoms; and $X_1$ represents a counter anion;

a compound shown by the following general formula [6]

wherein $R_{23}$ represents an alkyl group having 1 to 6 carbon atoms; $R_{24}$ to $R_{28}$ represent each independently a hydrogen atom or an alkyl group having 1 to 6 carbon atoms; and $X_2$ represents a counter anion;

a compound shown by the following general formula [7]

wherein $R_{29}$ to $R_{34}$ represent each independently a hydrogen atom or an alkyl group having 1 to 6 carbon atoms;

a compound shown by the following general formula [8]

In the formula [8], Z represents a nitrogen atom or a carbon atom; m represents an integer of 0 or 1, and when Z is a nitrogen atom, m represents 0, and when Z is a carbon atom, m represents 1; $R_{35}$ to $R_{39}$ represent each independently a hydrogen atom or an alkyl group having 1 to 6 carbon atoms.

That is, the present invention relates to (1) a method for converting non-methylated cytosine in a single-stranded DNA into uracil, comprising subjecting the single-stranded DNA to bisulfite reaction under the presence of at least one of compounds shown by the above-described general formula [1] to [8] (hereinafter, sometimes abbreviated as uracil conversion method of the present invention);

(2) a method for amplifying single-stranded DNA in which non-methylated cytosine has been converted into uracil, comprising further subjecting the single-stranded DNA after bisulfite reaction of (1) to PCR reaction (hereinafter, sometimes abbreviated as single-stranded DNA amplification method of the present invention); and (3) a method for detecting methylated cytosine in the aforementioned single-stranded DNA, comprising subjecting the single-stranded DNA amplified in (2) to nucleotide sequence analysis (hereinafter, sometimes abbreviated as a method for detecting methylated cytosine of the present invention) (hereinafter, the method of the above-described (1) to (3) sometimes abbreviated as a method of the present invention).

Effect of the Invention

According to the uracil conversion method of the present invention, non-methylated cytosine in a single-stranded DNA can be converted into uracil with high efficiency, and even in the case where the single-stranded DNA is a relatively long single-stranded DNA with 500 bp to 1000 bp, it can be converted with high efficiency. Further, since even if the bisulfite reaction is carried out in higher temperature the methylated cytosine will scarcely be deaminated, it would be possible to shorten the reaction time without decreasing detection accuracy of methylated cytosine. As a consequence, by amplifying a single-stranded DNA obtained by the uracil conversion method of the present invention and by analyzing the nucleotide sequence, detection of methylated cytosine in the single-stranded DNA can be performed with a high accuracy in a short period of time even if the single-stranded DNA is relatively large in length.

DETAILED DESCRIPTION OF THE INVENTION

Compound Shown by the General Formula [1] (Diamine Compound)

The alkyl group having 1 to 6 carbon atoms in $R_1$ to $R_6$ may be any of straight chain, branched chain or cyclic chain, and the one having 1 to 3 carbon atoms is preferable, specifically, for example, there are included a methyl group, an ethyl group, a n-propyl group, an isopropyl group, a n-butyl group, an isobutyl group, a sec-butyl group, a tert-butyl group, an n-pentyl group, an isopentyl group, a sec-pentyl group, a tert-pentyl group, a neopentyl group, a 2-methylbutyl group, a 1-ethylpropyl group, a n-hexyl group, an isohexyl group, a sec-hexyl group, a tert-hexyl group, a neohexyl group, a 2-methylpentyl group, a 3-methylpentyl group, a 1,2-dimethylbutyl group, a 2,2-dimethylbutyl group, a 1-ethylbutyl group, a 2-ethylbutyl group etc., and a methyl group, an ethyl group, a n-propyl group and an isopropyl group are preferable, and, a methyl group and an ethyl group are more preferable, and a methyl group is particularly preferable.

As $R_1$ to $R_6$, a hydrogen atom is preferable.

n is normally integer of 1 to 3, and 1 or 3 is preferable, and 3 is particularly preferable.

The compound shown by the general formula [1] includes, for example, the following formula [1-1] to [1-3], and, formula [1-1] and formula [1-3] are preferable, and formula [1-3] is more preferable.

Compound Shown by the General Formula [2] (Cyclic Amino Compound)

Y represents a carbon atom, an oxygen atom or a nitrogen atom; and a carbon atom or an oxygen atom is preferable, and a carbon atom is particularly preferable. In addition, when Y is an oxygen atom, k represents 0; when Y is a nitrogen atom, k represents 1; and when Y is a carbon atom, k represents 2.

The alkyl group having 1 to 6 carbon atoms in $R_7$ to $R_{12}$ includes the same ones as described above for the alkyl group having 1 to 6 carbon atoms in $R_1$ to $R_6$, and preferable one is also the same one as described above.

As $R_7$ to $R_{11}$, a hydrogen atom is preferable, and as $R_{12}$, the alkyl group having 1 to 6 carbon atoms is preferable, and an alkyl group having 1 to 3 carbon atoms is more preferable.

The compound shown by the general formula [2] includes, for example, the following formula [2-1] to [2-19], and, formula [2-1] to [2-4] are preferable, and formula [2-1] and [2-2] are more preferable.

[2-8]

[2-9]

[2-10]

[2-11]

[2-12]

[2-13]

[2-14]

[2-15]

[2-16]

[2-17]

[2-18]

[2-19]

Compound Shown by the General Formula [3] (Amino Compound)

The alkyl group having 1 to 6 carbon atoms in $R_{13}$ to $R_{15}$ may be any of straight chain, branched chain or cyclic chain, and the one which is straight chain or branched chain is preferable. An alkyl group having 2 to 6 carbon atoms is preferable, and the one having 2 to 4 carbon atoms is more preferable, specifically, for example, there are included an ethyl group, a n-propyl group, isopropyl group, a n-butyl group, an isobutyl group, a sec-butyl group, a tert-butyl group, a n-pentyl group, an isopentyl group, a sec-pentyl group, a tert-pentyl group, a neopentyl group, a 2-methyl-butyl group, a 1-ethylpropyl group, a n-hexyl group, an isohexyl group, a sec-hexyl group, a tert-hexyl group, a neohexyl group, 2-methylpentyl group, a 3-methylpentyl group, a 1,2-dimethylbutyl group, 2,2-dimethylbutyl group, a 1-ethylbutyl group, a 2-ethylbutyl group etc., and an ethyl group, a n-propyl group, an isopropyl group and a n-butyl group are preferable; an ethyl group, a n-propyl group and an isopropyl group are more preferable; an ethyl group and a isopropyl group are particularly preferable.

As $R_{13}$ to $R_{15}$, at least one of them is preferably the alkyl group having 1 to 6 carbon atoms, and more preferably, all of them are the alkyl group having 1 to 6 carbon atoms.

A compound shown by the general formula [3] includes primary amines such as ethylamine, propylamine, isopropylamine, butylamine, pentylamine, and hexylamine; secondary amines such as N-ethylmethylamine, N-methylpropylamine, N-butylmethylamine, N-hexylmethylamine, N-ethylpropylamine, and N-butylethylamine; tertiary amines such as trimethylamine, triethylamine, tripropylamine, triisopropylamine, tributylamine, N,N-dimethylethylamine, N,N-diethylmethylamine, and N-ethyldiisopropylamine; and tertiary amines are preferable, and among them, triethylamine, N-ethyldiisopropylamine, and triisopropylamine are preferable, and, triethylamine, and N-ethyldiisopropylamine are more preferable.

Compound Shown by the General Formula [4] (Pyridine Compound)

The alkyl group having 1 to 6 carbon atoms in $R_{16}$ to $R_{20}$ includes the same ones as described above for the alkyl group having 1 to 6 carbon atoms in $R_1$ to $R_6$, and preferable one is also the same one as described above.

A dialkylamino group having 2 to 6 carbon atoms in $R_{16}$, $R_{18}$ and $R_{20}$ includes, specifically for example, an amino group which is substituted by the alkyl group having 1 to 3 carbon atoms such as a dimethylamino group, a diethylamino group, a dipropylamino group, an ethylmethylamino group; and an amino group which is substituted by an alkyl group having 1 to 2 carbon atoms are preferable, and the dimethylamino group is particularly preferable.

$R_{17}$ and $R_{19}$ are preferable to be hydrogen atom, and $R_{16}$, $R_{18}$ and $R_{20}$ are preferable to be hydrogen, the alkyl group having 1 to 3 carbon atoms or the amino group substituted by the alkyl group having 1 to 2 carbon atoms.

The compound shown by the general formula [4] includes the following formula [4-1] to [4-14], and formula [4-1] to [4-4] are preferable, and formula [4-1], [4-2] and [4-4] are more preferable.

[4-1]

[4-2]

[4-3]

[4-4]

[4-5]

[4-6]

[4-7]

[4-8]

[4-9]

[4-10]

[4-11]

[4-12]

[4-13]

[4-14]

Compound Shown by the General Formula [5]

The alkyl group having 1 to 6 carbon atoms in $R_{21}$ or $R_{22}$ in the general formula [5] includes the same ones as described above for the alkyl group having 1 to 6 carbon atoms in $R_1$ to $R_6$, and preferable one is also the same one as described above.

$R_{21}$ is preferable to be the alkyl group having 1 to 3 carbon atoms, and $R_{22}$ is preferable to be the alkyl group having 2 to 6 carbon atoms, and an alkyl group having 2 to 3 carbon atoms is more preferable.

The counter anion for $X_1$ in the general formula [5] includes halogen ion such as fluorine ion, chlorine ion, bromine ion, iodine ion, and more specifically, includes $SbF_6^-$, $AsF_6^-$, $PF_6^-$, $BF_4^-$, $CF_3SO_2^-$, $CF_3CO_2^-$ and the like, and, $BF_4^-$, $CF_3SO_2^-$ and $CF_3CO_2^-$ etc. are preferable, and among them, $CF_3CO_2^-$ is particularly preferable.

The compound shown by the general formula [5] includes, specifically for example, the ones which are shown by formula [5-1] to [5-14] in the following Table 1; and, the ones which are shown by formula [5-1] to [5-4] are preferable, and the one which is shown by formula [5-1] or formula [5-2] is more preferable.

TABLE 1

| General formula | $R_{21}$ | $R_{22}$ | X |
|---|---|---|---|
| [5-1] | —$CH_3$ | —$C_2H_5$ | $CF_3CO_2^-$ |
| [5-2] | —$CH_3$ | —$C_2H_5$ | $CF_3SO_2^-$ |
| [5-3] | —$CH_3$ | —$C_2H_5$ | $PF_6^-$ |
| [5-4] | —$CH_3$ | —$C_2H_5$ | $BF_4^-$ |

TABLE 1-continued

| General formula | $R_{21}$ | $R_{22}$ | X |
|---|---|---|---|
| [5-5] | —$CH_3$ | —$C_2H_5$ | $SbF_6^-$ |
| [5-6] | —$CH_3$ | —$C_2H_5$ | $AsF_6^-$ |
| [5-7] | —$CH_3$ | —$C_3H_7$ | $CF_3CO_2^-$ |
| [5-8] | —$CH_3$ | —$C_3H_7$ | $CF_3SO_2^-$ |
| [5-9] | —$CH_3$ | —$C_4H_9$ | $CF_3CO_2^-$ |
| [5-10] | —$CH_3$ | —$C_4H_9$ | $CF_3SO_2^-$ |
| [5-11] | —$CH_3$ | —$C_5H_{11}$ | $CF_3CO_2^-$ |
| [5-12] | —$CH_3$ | —$C_5H_{11}$ | $CF_3SO_2^-$ |
| [5-13] | —$CH_3$ | —$C_6H_{13}$ | $CF_3CO_2^-$ |
| [5-14] | —$CH_3$ | —$C_6H_{13}$ | $CF_3SO_2^-$ |

Compound Shown by the General Formula [6]

The alkyl group having 1 to 6 carbon atoms in $R_{23}$ to $R_{28}$ in the general formula [6] may be any of straight chain, branched chain or cyclic chain; and the one which is straight chain or branched chain is preferable, and the one which has 1 to 4 carbon atoms is preferable. Specifically, for example, there are included a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 2-methylbutyl group, a 1-ethylpropyl group, a n-hexyl group, an isohexyl group, a sec-hexyl group, a tert-hexyl group, a neohexyl group, a 2-methylpentyl group, a 3-methylpentyl group, a 1,2-dimethylbutyl group, a 2,2-dimethylbutyl group, a 1-ethylbutyl group, a 2-ethylbutyl group etc., and among them, a methyl group, an ethyl group, a n-propyl group, an isopropyl group and a n-butyl group are preferable; and, a n-propyl group and a n-butyl group are more preferable.

As $R_{24}$ to $R_{28}$ in the general formula [6], a hydrogen atom is preferable.

$X_2$ in the general formula [6] includes the same one as $X_1$ in the general formula [5], and the preferable one includes also the same one.

The compound shown by the general formula [6] includes, specifically, for example, the ones which are shown by formula [6-1] to [6-16] in the following Table 2; and the ones which are shown by formula [6-1] to [6-4] are preferable, and the one which is shown by formula [6-1] or formula [6-2] is more preferable.

TABLE 2

| General formula | $R_{23}$ | $R_{24}$ | $R_{25}$ | $R_{26}$ | $R_{27}$ | $R_{28}$ | X |
|---|---|---|---|---|---|---|---|
| [6-1] | -$C_4H_9$ | -H | -H | -H | -H | -H | $CF_3CO_2^-$ |
| [6-2] | -$C_4H_9$ | -H | -H | -H | -H | -H | $CF_3SO_2^-$ |
| [6-3] | -$C_4H_9$ | -H | -H | -H | -H | -H | $PF_6^-$ |
| [6-4] | -$C_4H_9$ | -H | -H | -H | -H | -H | $BF_6^-$ |
| [6-5] | -$C_4H_9$ | -H | -H | -H | -H | -H | $SbF_6^-$ |
| [6-6] | -$C_4H_9$ | -H | -H | -H | -H | -H | $AsF_6^-$ |
| [6-7] | -$CH_3$ | -H | -H | -H | -H | -H | $CF_3CO_2^-$ |
| [6-8] | -$CH_3$ | -H | -H | -H | -H | -H | $CF_3SO_2^-$ |
| [6-9] | -$C_2H_5$ | -H | -H | -H | -H | -H | $CF_3CO_2^-$ |
| [6-10] | -$C_2H_5$ | -H | -H | -H | -H | -H | $CF_3SO_2^-$ |
| [6-11] | -$C_3H_7$ | -H | -H | -H | -H | -H | $CF_3CO_2^-$ |
| [6-12] | -$C_3H_7$ | -H | -H | -H | -H | -H | $CF_3SO_2^-$ |
| [6-13] | -$C_5H_{11}$ | -H | -H | -H | -H | -H | $CF_3CO_2^-$ |
| [6-14] | -$C_5H_{11}$ | -H | -H | -H | -H | -H | $CF_3SO_2^-$ |
| [6-15] | -$C_6H_{13}$ | -H | -H | -H | -H | -H | $CF_3CO_2^-$ |
| [6-16] | -$C_6H_{13}$ | -H | -H | -H | -H | -H | $CF_3SO_2^-$ |

Compound Shown by the General Formula [7] (DABCO Compound)

The alkyl group having 1 to 6 carbon atoms in $R_{29}$ or $R_{34}$ includes the same alkyl group having 1 to 6 carbon atoms in $R_1$ to $R_6$, and preferable one includes also the same one.

The compound shown by the general formula [7] includes, specifically, for example, the following formula [7-1] to [7-3], and formula [7-1] is preferable.

[7-1]

[7-2]

[7-3]

Compound Shown by the General Formula [8] (Pyrrole Compound)

The alkyl group having 1 to 6 carbon atoms in $R_{35}$ or $R_{39}$ includes the same alkyl group having 1 to 6 carbon atoms in $R_1$ to $R_6$, and preferable one includes also the same one.

As $R_{36}$ to $R_{39}$, a hydrogen atom is preferable.

Z represents a nitrogen atom or a carbon atom; and a nitrogen atom is preferable. It should be noted that, when Z is a nitrogen atom, m represents 0, and when Z is carbon atom, m represents 1.

A specific example of the compound shown by the general formula [8] includes, for example, the following formula [8-1] to [8-8]; and, the formula [8-1] to [8-4] are preferable, the formula [8-1] to [8-2] are more preferable, and the formula [8-1] is further preferable.

[8-1]

[8-2]

[8-3]

[8-4]

[8-5]

[8-6]

[8-7]

[8-8]

In the method of the present invention, at least one of compounds shown by the above-described general formula [1] to [8] may make exist at the time of bisulfite reaction, and considering the efficiency of conversion from non-methylated cytosine into uracil, among the compounds shown by the above-described general formula [1] to [8], the compounds shown by the general formula [1] to [3] are preferable, the compound shown by the general formula [1] or [2] is more preferable, and the compound shown by the general formula [1] is particularly preferable.

As a single-stranded DNA pertaining to the present invention, a single-stranded DNA containing methylated cytosine is preferable, and the one, which has a promoter region where the content rate of methylated cytosine is high, is preferable. The above single-stranded DNA may be either known sequence or unknown sequence. In the case of unknown sequence, the nucleotide sequence of the single-stranded DNA before being subjected to the bisulfite reaction has to be analyzed its nucleotide sequence, therefore, the known sequence is preferable. The number of base of said single-stranded DNA is usually 80 to 1000 bases, preferably it is 100 to 600 bases.

The single-stranded DNA pertaining to the present invention can be obtained, according to well-known DNA extraction methods such as alkaline SDS method described in, for example, "Labo Manual for Genetic Engineering" (Maruzen Co., Ltd.) and "Handbook of Gene Technology" (Yodosha Co., Ltd.) etc., alternatively, by extracting from a cell, a microorganism, a virus, and the like using a commercially available extraction kit of genomic DNA. It should be noted that, in the case where the extracted DNA is double stranded, single-stranded DNA can be obtained by the well known per se single strand formation treatment.

Said single strand formation treatment includes, for example, a heat treatment performed at usually 80 to 100° C., preferably at 85 to 95° C. for usually 30 seconds to 10 minutes, preferably for 1 to 3 minutes, or an alkaline treatment performed by contacting the DNA with alkaline circumstances, etc. In the method of the present invention, since even if the temperature at the bisulfite reaction is increased to 80 to 100° C., the reaction can be performed without degrading the DNA, the single strand formation treatment and the bisulfite reaction can be performed simultaneously by subjecting the double-stranded DNA to the bisulfite reaction at 80 to 100° C.; and since this makes the treatment simple, when the single strand formation treatment is performed, said heat treatment is preferable. The above-described alkaline treatment is carried out, specifically, for example, by adding alkali or its aqueous solution to the DNA pertaining to the present invention or a solution containing the DNA pertaining to the present invention to make the solution alkaline to usually pH 10 to 14, preferably pH 12 to 14. Said alkali includes, for example, alkali metal hydroxide such as sodium hydroxide and potassium hydroxide; alkaline-earth metal hydroxide such as barium hydroxide, magnesium hydroxide, and calcium hydroxide; alkaline metal carbonate such as sodium carbonate; ammonia, and amines and the like. Among them, alkali metal hydroxide such as sodium hydroxide and potassium hydroxide is preferable, and among these, sodium hydroxide is particularly preferable.

[A method for converting non-methylated cytosine in a single-stranded DNA of the present invention into uracil (A uracil conversion method of the present invention)]

The uracil conversion method of the present invention may be performed by subjecting a single-stranded DNA to bisulfite reaction under the presence of at least one of the compounds shown by the above-described general formula [1] to [8].

The above-described bisulfite reaction may be performed according to the bisulfite reaction usually used in this field, except that at least one compound selected from the compounds shown by the above-described general formula [1] to [8] is coexisted in the reaction solution. Specifically, for example, the single-stranded DNA is reacted with sulfite under existence of a compound shown by the general formula [1] to [8] (sulfonation of cytosine), then the sulfonated cytosine is hydrolyzed, and further, desulfonated under existence of alkali. According to said reaction, the methylated cytosine is not reacted and kept as it is, and only non-methylated cytosine is converted into uracil. It should be noted that the compound shown by the general formula [1] to [8] is preferable to be existed at the time of reaction with sulfite and hydrolysis treatment.

In the above-described bisulfite reaction, usually a single-stranded DNA is provided as a solution in which the single-stranded DNA has been dissolved, and said solution includes, for example, Good's buffer solution such as MES and HEPES, phosphate buffer solution, Tris buffer solution, glycine buffer solution, borate buffer solution, sodium bicarbonate buffer solution, and sterile water, etc. of pH 6 to 8; and among them, sterile water is preferable. The DNA amount in said solution is not limited specifically, but usually it is 10 to 100 ng in 1 to 10 µL of the solution.

Usage of the compound shown by the above-described general formula [1] to [8], since the sulfite will precipitate if the amount of these compounds is large, in the case where these compounds are liquid, may be an amount which provide concentration in the reaction solution to be usually 1 to 10%, preferably 3 to 10%, more preferably 3 to 8%. In addition, in the case where these compounds are solid, the usage may be an amount which provides concentration in the reaction solution to be usually 1 to 1000 mmol/L, preferably 1 to 500 mmol/L, more preferably 10 to 300 mmol/L.

The sulfite in the reaction of DNA with sulfite in the above-described bisulfite reaction includes, for example, sodium bisulfite and ammonium sulfite, and sodium bisulfite is preferable. Usually, the usage thereof is added so that the final concentration in the reaction solution gives 1 to 6 mol/L relative to 1 to 500 µL of a solution containing 50 to 500 ng of DNA. The reaction of said DNA with sulfite is performed usually by reacting at 30 to 100° C., preferably at 50 to 100° C., more preferably at 80 to 95° C., and usually for 60 minutes to 20 hours, preferably for 60 minutes to 5 hours, more preferably for 60 to 120 minutes.

The hydrolysis of sulfonated cytosine during the above-described bisulfite reaction is not limited specifically as long as it is a method usually performed in this field, and usually it is performed by heating at 30 to 100° C., preferably at 80 to 95° C., and usually for 60 minutes to 20 hours, preferably for 60 minutes to 5 hours, more preferably for 60 to 120 minutes. It should be noted that said hydrolysis treatment may be performed simultaneously with the above-described reaction of DNA with the sulfite. In that case, the reaction temperature and the reaction time in the reaction of DNA with sulfite may be set according to the hydrolysis condition of the sulfonated cytosine.

With respect to the DNA which carried out the above-described hydrolysis, it is preferable to subject it to purification treatment before desulfonation treatment. Said purification treatment is the treatment to be carried out for removing high-concentration of sulfite salt to be used in the bisulfite reaction, and it may be carried out according to the method for purifying DNA to be carried out usually in this field. Specifically, there are included for example, a method in which chaotropic agent such as guanidine hydrochloride or sodium iodide is added to the DNA or a solution containing DNA, and it is separated and purified by HPLC method etc.; for example, extraction and purification by a mixed solution of phenol/chloroform/isoamyl alcohol; alcohol precipitation method; purification by a column filled with silica gel; filtration method with filter, etc.; among them, the alcohol precipitation method is preferable. Said alcohol precipitation method is specifically performed as follows.

That is, to a 10 µL of solution containing the DNA after hydrolysis, usually, 40 to 110 µL of alcohol and 30 to 100 µL of buffer solution are added, and centrifugal separation is carried out. After centrifugal separation, by removing supernatant and washing with alcohol, the DNA can be separated and purified. At the time when the above-described alcohol and buffer solution are added, to facilitate the removal of supernatant solution after separation, 0.1 to 1 µL of Ethachinmate or glycogen per 10 µL of the solution containing DNA may be added. The above-described alcohol includes ethanol, isopropanol, butanol, and the like; and, isopropanol is particularly preferable. In the bisulfite reaction pertaining to the present invention, although the reason is unclear, when isopropanol is used, only the DNA can be precipitated efficiently and it will become possible to advance the reaction efficiently. The above described buffer solution includes, for example, Good's buffer solution such as MES and HEPES, phosphate buffer solution, Tris buffer solution, glycine buffer solution, borate buffer solution, and sodium bicarbonate buffer solution and so on; and among them, Good's buffer solution such as MES and HEPES, Tris buffer solution, etc. are preferable, and Tris buffer solution is particularly preferable. The pH of these buffer solutions is usually pH 7 to 8, preferably pH 7 to 7.5, and concentration of buffering agent in the buffer solution is usually in the range of 0.1 to 5 mol/L, preferably 0.1 to 2 mol/L. The above-described centrifugal separation is not limited specifically, as long as it is an aspect to be carried out usually in this field, and usually it is carried out by 12,000 to 22,000 g for 10 to 30 minutes.

The desulfonation reaction in the above-described bisulfite reaction includes the same method as alkaline treatment in the section of the above-described single strand formation treatment, and preferable aspect also includes the same one. Specifically, for example, it may be performed as follows.

That is, the desulfonation reaction is performed by adding usually 1 to 10 µL, preferably 1 to 5 µL of 0.5 to 3 mol/L aqueous alkaline solution to a 10 µL of the solution after hydrolysis treatment or a solution subjected to purification treatment after hydrolysis treatment, and by warming the solution usually at 25 to 70° C., preferably at 30 to 50° C., usually for 5 to 60 minutes, preferably for 5 to 30 minutes.

A preferable example of the method for converting non-methylated cytosine in a single-stranded DNA into uracil of the present invention will be explained below.

That is, for example, DNA is extracted from cell and the like using a DNA extraction kit and the like, then 1 µg of the DNA is dissolved, for example, in 5 to 15 µL of sterile water. To 3 to 5 µL of said solution, for example, 50 to 100 µL of 2 to 5 mol/L sodium bisulfite (pH 5.0 to 7.0), and the compound shown by the general formula [1] to [8] or 1 to 12 µL of aqueous solution containing them are added so as to provide a concentration in reaction solution of 3 to 10% when the compounds shown by the general formula [1] to [8] are liquid, or added so as to provide a concentration in reaction solution of 1 to 1000 mmol/L when the compounds shown by the general formula [1] to [8] are solid, and then the solution is heated at 80 to 100° C. for 60 to 120 minutes. In the case where the DNA is double-stranded, the double-stranded DNA is made single-stranded DNA by reacting under said condition, and cytosine in said single-stranded DNA is sulfonated, and at the same time, the sulfonated cytosine can be hydrolyzed. Subsequently, 1 mol/L Tris buffer solution (pH 7.0 to 8.0) and isopropanol are added in 5 to 10 times larger volume than the solution after hydrolysis in a ratio of 40:60 to 60:40, preferably by a ratio of 40:60 to 50:50, respectively, to precipitate the single-stranded DNA after hydrolysis. On this occasion, if 1 to 3 µL of Ethachinmate or glycogen is added, confirmation of DNA precipitation become easy. After that, centrifugal separation is performed by 12,000 to 20,000 g for 10 to 20 minutes, then the supernatant solution is removed, and the obtained DNA is washed with ethanol. Thereby, the DNA after hydrolysis can be extracted and purified. Further, 1 µg of the obtained DNA is dissolved, for example, in 30 to 40 µL of sterile water, and to said solution, 5 to 20 µL of 1 to 3 mol/L sodium hydroxide is added and reacted at 30 to 40° C. for 20 to 60 minutes to desulfonate. After that, if necessary, the purification is performed by removing low molecular weight DNA using, for example, a commercially available kit and the like. Thereby, the bisulfite reaction pertaining to the present invention is completed, and a DNA, in which non-methylated cytosine in a single-stranded DNA has been uracilated efficiently, (hereinafter, sometimes abbreviated as uracilated DNA) can be obtained.

[A Method for Amplifying Single-Stranded DNA of the Present Invention]

A method for amplifying single-stranded DNA of the present invention is performed by subjecting the uracilated DNA (bisulfite reaction product) obtained by the above-described uracil conversion method of the present invention to PCR reaction, and by said method, the single-stranded DNA in which non-methylated cytosine has been converted into uracil is amplified.

The PCR reaction in the method for amplifying single-stranded DNA of the present invention may be carried out according to the method well known per se, for example, the method described in Nucleic Acids Research, 1991, Vol. 19, 3749, BioTechniques, 1994, Vol. 16, 1134-1137, and specifically, it is carried out as follows. That is, to 1 to 100 ng of quantity of nucleic acid of uracilated DNA which will becomes a template; usually 0.1 to 100 pmol, preferably 0.1 to 50 pmol of 2 kinds of primers, respectively; usually 1 to 10 Units, preferably 2.5 to 5 Units of DNA polymerase; and usually 0.01 to 20 μmol, preferably 0.01 to 10 μmol of a mixture of 4 kinds of deoxyribonucleotide triphosphate (dNTPs) are added; and, for example, by setting the processes of (1) at 93 to 98° C. for 1 to 10 minutes→(2) at 93 to 98° C. for 10 to 30 seconds→(3) at 50 to 60° C. for 10 to 30 seconds→(4) at 68 to 72° C. for 30 seconds to 5 minutes as 1 cycle, and by carrying out for 20 to 40 cycles in a buffer solution such as Tricine buffer solution or Tris buffer solution of pH 7 to 9, the uracilated DNA can be amplified and obtained. It should be noted that, according to the DNA polymerase to be used, after performing the above-described cycles, heating at 68 to 72° C. for 1 to 5 minutes may be performed for 3' adenine addition In the above-described PCR reaction, after the reaction, it is preferable to purify the obtained DNA by purification method to be used usually in this field, such as, for example, extraction by a mixed solution of phenol/chloroform/isoamyl alcohol, alcohol precipitation, column purification, filtration by a filter, etc. In addition, after the above-described purification, it is more preferable to extract DNA having objective base pair (bp). Said extraction method includes the method well known per se, for example, the method using agarose gel electrophoresis, the method using liquid chromatography, and the method using electrophoresis on polyacrylamide gel and the like as described in Labo Manual for Genetic Engineering, Expanded Edition. In addition, the double-stranded DNA pertaining to the present invention which is obtained by the above-described PCR reaction may be subjected to further PCR reaction to obtain more amount of the objective DNA.

Two kinds of primers in the above-described PCR reaction may be the one which includes a part of uracilated DNA, which is a template, and may be used appropriately depending on the single-stranded DNA pertaining to the present invention by selecting primers to be used usually in this field. The number of nucleotides thereof is usually 12 to 40, preferably 15 to 35, more preferably 18 to 32.

The DNA polymerase in the above-described PCR reaction may be any DNA polymerase as long as it is usually used in this field, and, the one which has 5'→3' polymerase activity is preferable, and among them, the one which has exonuclease activity but does not have 3'→5' exonuclease activity is more preferable. Specifically, for example, mutant type Taq DNA polymerase such as KAPA2G polymerase, Taq DNA polymerase, and Tth DNA polymerase are preferable, and among them, KAPA2G polymerase is particularly preferable.

The above-described dNTPs is not limited specifically as long as it is a mixture of 4 kinds of deoxyribonucleotide triphosphate (dATP, dCTP, dGTP, dTTP) usually employed in this field.

A preferable example of the method for amplifying DNA of the present invention is explained below.

That is, first, as described in the section of the uracil conversion method of the present invention, by subjecting a single-stranded DNA to the bisulfite reaction, the uracilated DNA is obtained. After that, the obtained DNA is subjected to the PCR reaction. That is, to 1 to 3 μL of a solution containing 1 to 100 ng of single-stranded DNA obtained by the bisulfite reaction, 5 to 10 μL of 1 to 10 μmol/L primer for upstream of the DNA of amplification target and 5 to 10 μL of 1 to 10 μmol/L primer for downstream of the DNA of amplification target, 5 to 10 μL of a mixture of 4 kinds of 1 to 5 mmol/L deoxyribonucleotide triphosphate (dNTPs), and 10 to 20 μL of 1 to 5 Units KAPA DNA polymerase are added; and then, for example, by setting the reactions at 93 to 98° C. for 1 to 10 minutes→at 93 to 98° C. for 10 to 30 seconds→at 50 to 60° C. for 10 to 30 seconds→at 68 to 72° C. for 30 seconds to 5 minutes as 1 cycle, 20 to 40 cycles of reaction are carried out. Thereby, the uracilated DNA is amplified. It should be noted that, when the adenine-addition activity of 3'-terminal of DNA polymerase is utilized for the purpose of employing a TA cloning method as a method for incorporating the uracilated DNA into a vector to be described in later, after completing the above-described reaction cycles, further heating at 68 to 72° C. for 30 seconds to 5 minutes may be carried out. After that, said double-stranded DNA is subjected to electrophoresis with the use of, for example, agarose gel or non-denaturing polyacrylamide gel, and the DNA of desired chain length is extracted. It should be noted that, if needed, the obtained DNA may be purified, for example, by extraction with a mixed solution of phenol/chloroform/isoamyl alcohol. By the above procedure, the uracilated DNA can be amplified efficiently.

[A Method for Detecting Methylated Cytosine of the Present Invention]

The method for detecting methylated cytosine of the present invention is performed by subjecting the amplified uracilated DNA (PCR reaction product) obtained by the method for amplifying single-stranded DNA of the present invention to nucleotide sequence analysis.

As the above-described nucleotide sequence analysis, there is no particular limitation as long as it is a method for analyzing nucleotide sequence usually employed in this field. For example, it may be carried out according to a routine procedure such as a fluorescent dye terminator sequencing method and Sanger's method which are described in Lab Manual for Genetic Engineering, and Handbook of Gene Technology, etc. Specifically, for example, the uracilatd DNA, which is obtained by the amplification method of the present invention, is incorporated in a vector; and the obtained recombinant vector is transfected into competent cell; said competent cell is cultured; and from there, a plasmid including uracilated DNA is extracted; and using said plasmid, decoding is performed by, for example, a sequencer and the like. By comparing thus obtained nucleotide sequence with the nucleotide sequence of normal DNA which has not been subjected to the bisulfite reaction, methylated cytosine can be detected. That is, in the bisulfite reaction pertaining to the present invention, since all cytosine except for methylated cytosine are converted into uracil, the methylated cytosine can be detected by finding out cytosine not converted into uracil in the obtained nucleotide sequence.

The method for incorporating the above-described uracilated DNA into a vector includes, specifically, for example, a method for inserting uracilated DNA into a vector using T4 DNA ligase after the vector such as plasmid, cosmid, and phagemid, as well as uracilated DNA are blunt-ended by T4 DNA polymerase and the like, or a TA cloning method in which adenine (A) is added to the uracilated DNA, and then said adenine-added uracilated DNA is incorporated into a thymine base-added vector using T4 DNA ligase. Among them, the TA cloning method is preferable because it does not require cleaving both DNA to be inserted and a vector by restriction enzyme, and it is simple.

Said TA cloning method is performed, specifically, for example as follows. That is, to 100 ng of uracilated DNA after PCR reaction, 1 to 5 Units of Taq DNA polymerase is added, and reacted at 55 to 75° C. for 10 to 30 minutes, and adenine is added to 3'-terminal of uracilated DNA. It should be noted that, on the occasion of the PCR reaction, when DNA polymerase having 3'-terminal adenine-adding activity is employed, the above-described adenine addition step is not necessary. In addition, on the occasion of said reaction, 0.01 to 20 nmol of dATP relative to 100 ng of uracilated DNA may be added to the reaction solution, and when the PCR reaction solution is used for TA cloning as it is, since the dATP is still remaining, the addition of dATP is not necessary. In addition, with respect to the adenine-added uracilated DNA, after synthetic reaction, it is preferable to purify the obtained DNA by a method such as extraction with a mixed solution of phenol/chloroform/isoamyl alcohol, alcohol precipitation, column purification, and filtration by a filter, etc. Subsequently, to 10 to 100 ng of the adenine-added uracilated DNA, thymine base-added vector for E. coli transformation and 300 to 3000 Units of T4 DNA ligase are added, and by reacting at 10 to 40° C. for 30 to 90 minutes, a recombinant vector, in which the uracilated DNA is incorporated, can be obtained.

A method for transforming the above-described recombinant vector to competent cell includes, for example, a heat shock method by heating at 35 to 45° C. for 20 to 90 seconds, and an electroporation method in which 1.5 to 2.5 kV of electric pulse, and so on are applied. As the competent cell to be used herein, if it is E. coli or B. subtilis, which is usually used, any one of them can be employed, and its usage may be set appropriately within the range usually employed.

Cultivation of the above-described competent cell is performed, for example, on a medium such as LB agar medium containing 30 to 150 µg/mL of ampicillin, or M9 agar medium containing 30 to 150 µg/mL of ampicillin, at 30 to 40° C. for 12 to 20 hours. It should be noted that, as the above-described medium, either one of natural medium or synthetic medium etc. may be employed as long as it contains carbon source, nitrogen source and inorganic salts, which become nutritional source of bacteria, and yeast extract as a growth factor, and it enables to culture the transformant cell efficiently. Said carbon source includes carbohydrates such as glucose, fructose, sucrose and starch; organic acids such as acetic acid and propionic acid, and alcohols such as ethanol and propanol. Said nitrogen source includes ammonia; ammonium salt of inorganic acid or organic acid such as ammonium chloride, ammonium sulfate, ammonium acetate, and ammonium phosphate; or in addition to other nitrogen-containing compounds, peptone, tryptone, meat extract, and Corn Steep Liquor, and the like. The inorganic salts include monobasic potassium phosphate, dibasic potassium phosphate, magnesium phosphate, magnesium sulfate, sodium chloride, ferrous sulfate, manganese sulfate, copper sulfate, and calcium carbonate, etc.

As a method for extracting a plasmid including the uracilated DNA from cultured competent cell, for example, first, the DNA derived from plasmid, which includes the uracilated DNA in a colony, is amplified by colony PCR method. After that, colonies are determined whether the objective plasmid is amplified in the colony, for example, by electrophoresis, and from the colony, which is identified insertion of objective plasmid, the objective plasmid is extracted.

Said colony PCR method is carried out, for example, as follows. That is, to the cultured colony, usually each 0.1 to 100 pmol, preferably 0.1 to 50 pmol of 2 kinds of PCR primers for detection of objective nucleotide sequence, respectively, usually 0.01 to 20 nmol, preferably 0.01 to 10 nmol of 4 kinds of mixed deoxyribonucleotide triphosphate (dNTPs), and usually 1 to 10 Units, preferably 1 to 5 Units of DNA polymerase are added; and in a buffer solution such as Tricine buffer solution, Tris hydrochloric acid buffer solution and the like of pH 7 to 9, and, for example, by setting the reactions (1) at 93 to 98° C. for 1 to 10 minutes→(2) at 93 to 98° C. for 10 to 30 seconds (3) at 50 to 60° C. for 10 to 30 seconds→(4) at 68 to 72° C. for 30 seconds to 5 minutes as 1 cycle, 25 to 40 cycles of reaction are carried out. The above-described 2 kinds of primer include the one which is designed to be able to amplify the objective DNA, namely, the one which includes the entire or a part of uracilated DNA, or the sequences derived from vector which locate at both end of the inserted uracilated DNA, and the sequences derived from vector, which locate at both end of the uracilated DNA, are preferable. That is, in the method for amplifying DNA of the present invention and in the method for detecting methylated cytosine of the present invention, since non-methylated cytosine is uracilated, and said uracil is read as thymine at the time of the PCR reaction, if all cytosine were non-methylated cytosine, the uracilated DNA would be consisted of 3 nucleotides. Therefore, in order to carry out the PCR reaction efficiently, the sequences originated in the vector and located at the both ends of the uracilated DNA, which can be constituted by 4 nucleotides, are preferable. The number of nucleotides of the above-described primer is usually 12 to 30, preferably 15 to 25, more preferably 18 to 22. The above-described DNA polymerase may be any DNA polymerase as long as it is usually employed in this field, and specifically, for example, there are included Taq DNA polymerase, Tth DNA polymerase, and KOD DNA polymerase, etc., and among them, Taq DNA polymerase and KOD DNA polymerase, etc. are preferable.

The electrophoresis method to be carried out after the above-described colony PCR reaction may be any electrophoresis method, which is usually employed in this field, as long as it can determine the number of bases from the mobility; and agarose gel electrophoresis method is preferable. It should be noted that, the electrophoretic condition in said electrophoresis method may be set appropriately according to well-known method.

As the method for taking out plasmid from the above-described colony part, plasmid may be extracted by a well-known plasmid extraction method such as alkaline SDS method, after shaking culture, for example, as described in Lab Manual for Genetic Engineering (Maruzen Co., Ltd.), and Handbook of Gene Technology (Yodosha Co., Ltd.). It should be noted that, extraction of plasmid may be carried out using commercially available kit. As the culture medium in the above-described shaking culture, the same medium as described in the section of cultivation of competent cell can be used except for making solution without using agarose, and preferable cultivation time and cultivation temperature are also the same range as described in the section of cultivation of competent cell.

Preferable example of the method for detecting methylated cytosine of the present invention is explained below.

That is, first, as described in the sections of the uracil conversion method of the present invention and the amplification method of the present invention, by subjecting a single-stranded DNA to the bisulfite reaction and the PCR reaction in this order, amplified uracilated DNA is obtained. To 1 to 5 µL of sterile water containing 10 to 100 ng of said uracilated DNA, 1 to 3 µL of 10 to 100 ng of a thymine-added vector for E. coli transformation, and 1 to 3 µL of 300 to 3000 Units of T4 DNA ligase are added, and reacted at 10 to 20° C. for 30 to 240 minutes to obtain a recombinant vector which has been incorporated with the uracilated DNA. It should be noted that, in the case where a DNA polymerase which does not have adenine addition activity at the time of the PCR reaction, for example, α-DNA polymerase, is employed, adenine is added to the uracilated DNA before being incorporated into a vector. Said adenine addition method may be performed, for example, by adding 0.5 to 1 μL of 1 to 5 Units Taq DNA polymerase to 5 to 10 μL of PCR reaction solution containing 100 ng to 1 μg of uracilated DNA, and reacting at 55 to 75° C. for 10 to 30 minutes to add adenine on the 3'-terminal of the uracilated DNA. It should be noted that, after adenine addition reaction, it is preferable to be subjected to purification treatment. After obtaining recombinant vector, 10 to 100 ng of the obtained recombinant vector is added to $10^8$ to $10^9$ cells of competent cell, and transformation is carried out by heating at 35 to 45° C. for 20 to 90 seconds. Furthermore, the cells are cultured, for example, on an agar medium containing 30 to 150 μg/mL of ampicillin, 1% (w/v) of tryptone, 0.5% (w/v) of yeast extract, and 1% (w/v) of sodium chloride at 30° C. to 40° C. for 12 hours to 20 hours. Next, the obtained culture is subjected to the colony PCR. Specifically, to 1 μL to 10 μL of sterile water in which colony has been dissolved, 1 to 5 μL of 2 kinds of 1 to 10 μmol/L of primers, which are designed to be able to amplify the objective DNA, respectively, usually 1 to 5 μL of 1 to 5 mmol/L of 4 kinds of mixed deoxyribonucleotide triphosphate (dNTPs) and 0.5 to 1 μL of 1 to 5 Units Taq DNA polymerase are added, and reacted in a buffer solution such as Tricine buffer solution and Tris hydrochloric acid buffer solution of pH 7 to 9, for example, by setting the reactions (1) at 93 to 98° C. for 1 to 10 minutes→(2) at 93 to 98° C. for 10 to 30 seconds→(3) at 50 to 60° C. for 10 to 30 seconds→(4) at 68 to 72° C. for 30 seconds to 5 minutes as 1 cycle, 30 cycles to 40 cycles of reaction are performed. After that, existence of the objective DNA in the colony is determined by agarose gel electrophoresis, and identified colonies are collected. After carrying out shaking culture of the collected colonies in LB medium, the objective DNA is taken out from the culture medium using, for example, commercially available plasmid extraction kit and the like, and nucleotide sequence of the DNA is decoded by a sequencer, etc. Comparing the obtained sequence with the normal nucleotide sequence which is not subjected to the bisulfite reaction, and by finding out the cytosine which is not uracilated in the decoded nucleotide sequence, the methylated cytosine can be detected.

Hereinafter, the present invention will be explained in more detail by referring to Experimental Example, Example, and Comparative Examples and so on, and the present invention is not limited thereto in any way.

EXAMPLE

Example 1 to 16, Comparative Example 1 to 2

PCR Amplification of DNA Obtained by Uracil Conversion Method of the Present Invention and Conventional Bisulfite Reaction (1) Extraction of Mouse Genomic DNA Using QuickGene SP kit DNA tissue (produced by Fuji Film Co., Ltd.), genomic DNA was extracted from $1\times10^6$ cells of mouse embryonic stem cell (ES cell) according to an instruction manual.

(2) Bisulfite Reaction The genomic DNA (360 ng) obtained in the above-described (1) was dissolved in 4 μL of sterile water. Said solution was prepared in 17 tubes, and to each of them, 90 μL of 3.5 mmol/L sodium bisulfite aqueous solution (pH 5.2) (produced by Wako Pure Chemical Industries Co., Ltd.), and 6 μL of the following compound in Table 3 or 6 μL of aqueous solution with a concentration described in Table 3 were added and mixed (total volume: 100 μL). Then, the mixture was incubated at 95° C. for 2 hours. After that, 400 μL of 1 mol/L Tris-hydrochloride buffer solution (pH 7.0) (produced by Nippon Gene Co., Ltd.), 1 μL of glycogen (produced by Wako Pure Chemical Industries Co., Ltd.), and 500 μL of isopropanol (produced by Wako Pure Chemical Industries Co., Ltd.) were added and mixed, and centrifugal separation was performed by 18800×g for 5 minutes. After removal of supernatant and it was washed with 75% ethanol (produced by Wako Pure Chemical Industries Co., Ltd.), each was dissolved in 40 μL of sterile water.

TABLE 3

| Example | Name of compound | Additive volume or concentration |
|---|---|---|
| Example 1 | 1,8-Diazabicyclo[5.4.0]undeca-7-ene (DBU) (produced by Wako Pure Chemical Industries Co., Ltd.) | 6 μL |
| Example 2 | 1,5-Diazabicyclo[4.3.0]none-5-ene (DBN) (produced by Wako Pure Chemical Industries Co., Ltd.) | 6 μL |
| Example 3 | 1,4-Diazabicyclo(2,2,2)octane (DABCO) (produced by Wako Pure Chemical Industries Co., Ltd.) | 1 mol/L aqueous solution, 6 μL |
| Example 4 | Imidazole (produced by Wako Pure Chemical Industries Co., Ltd.) | 1 mol/L aqueous solution, 6 μL |
| Example 5 | 4-Dimethylaminopyridine (DMAP) (produced by Wako Pure Chemical Industries Co., Ltd.) | 1 mol/L aqueous solution, 6 μL |
| Example 6 | 1-Ethyl-3-methylimidazolium trifluoromethanesulfonate (ionic liquid $CF_3SO_3$-type) (produced by Wako Pure Chemical Industries Co., Ltd.) | 6 μL |
| Example 7 | 1-Ethyl-3-methylimidazolium trifluoroacetate (ionic liquid $CF_3CO_2$-type) (produced by Wako Pure Chemical Industries Co., Ltd.) | 6 μL |
| Example 8 | 1-Ethyl-3-methylimidazolium tetrafluoroborate (ionic liquid $BF_4$-type) (produced by Wako Pure Chemical Industries Co., Ltd.) | 6 μL |

TABLE 3-continued

| Example | Name of compound | Additive volume or concentration |
|---|---|---|
| Example 9 | Pyridine (produced by Wako Pure Chemical Industries Co., Ltd.) | 6 μL |
| Example 10 | 2,4,6-Trimethylpyridine (produced by Wako Pure Chemical Industries Co., Ltd.) | 6 μL |
| Example 11 | Piperidine (produced by Wako Pure Chemical Industries Co., Ltd.) | 6 μL |
| Example 12 | 1-Methylpiperidine (produced by Wako Pure Chemical Industries Co., Ltd.) | 6 μL |
| Example 13 | Morpholine (produced by Wako Pure Chemical Industries Co., Ltd.) | 6 μL |
| Example 14 | 4-Methylmorpholine (produced by Wako Pure Chemical Industries Co., Ltd.) | 6 μL |
| Example 15 | Triethylamine (produced by Wako Pure Chemical Industries Co., Ltd.) | 6 μL |
| Example 16 | N-Ethyldiisopropylamine (produced by Wako Pure Chemical Industries Co., Ltd.) | 6 μL |
| Comparative Example 1 | Absent | — |
| Comparative Example 2 | Hydroquinone (produced by Wako Pure Chemical Industries Co., Ltd.) | 0.2 mol/L aqueous solution |

To each 40 μL of sterile water in which the above-described reactant was dissolved, 10 μL of 1 mol/L sodium hydroxide (produced by Wako Pure Chemical Industries Co., Ltd.) was added and mixed, and incubated at 40° C. for 10 minutes to carry out the desulfonation reaction. After that, 1 μL of 10 mol/L ammonium acetate (produced by Nippon Gene Co., Ltd.) was added and mixed, and further 51 μL of isopropanol (produced by Wako Pure Chemical Industries Co., Ltd.) was added and mixed, and centrifugal separation was performed by 18800×g for 5 minutes under room temperature. Subsequently, the supernatant solution was removed and after washing with 75% ethanol, it was dried and dissolved in 25 μL of sterile water. Further, in order to remove low molecular weight DNA and dNTPs, 25 μL of DNA cleaner (produced by Wako Pure Chemical Industries Co., Ltd.) was added and mixed, and after leaving it at room temperature for 5 minutes, centrifugal separation was performed by 14000×g for 5 minutes under room temperature. Finally, the supernatant was removed and washed with 75% ethanol, and after drying, it was dissolved in 9 μL of sterile water, respectively.

(3) PCR amplification reaction

Each 1 μL of a solution containing bisulfite reaction product (uracilated DNA) obtained in (2) was placed in a PCR tube, and further, 10 μL of 5×KAPA2G BUFFER A (Kapa Biosystems Inc.), 1 μL of 10 mmol/L dNTPs mixed solution (produced by TOYOBO Co. Ltd.), 31.5 μL of sterile water, and each 3 μL of 5 μL PCR primer Forward solution and Reverse solution for Fgf4 gene [Forward: 5'GGT-TGGGGTTTTTTTAGGTGATAGTAG3' (SEQ ID NO: 1) (GenBank Accession No. AC149593: derived from 230224-230250), Reverse: 5'CCTTTTAAAAC-CCAACAAATAATCCCCTAC3' (SEQ ID NO: 2) (Gen-Bank Accession No. AC149593: derived from 230715-230744were added for each, and mixed gently on ice. Subsequently, after heating at 94° C. for 30 seconds, the reactions at 94° C. for 20 seconds → at 58° C. for 20 seconds → at 72° C. for 30 seconds were set as 1 cycle, 35 cycles were carried out, and finally heated at 72° C. for 1 minute, and thus the PCR reaction was carried out. After that, the obtained PCR-amplified products were fractionated by electrophoresis using 1.5% agarose gel (Example 1 to 8) or by Agilent 2100 bioanalyzer (Agilent Technologies, Inc.), and whether the objective DNA was amplified was confirmed.

Figure 1:
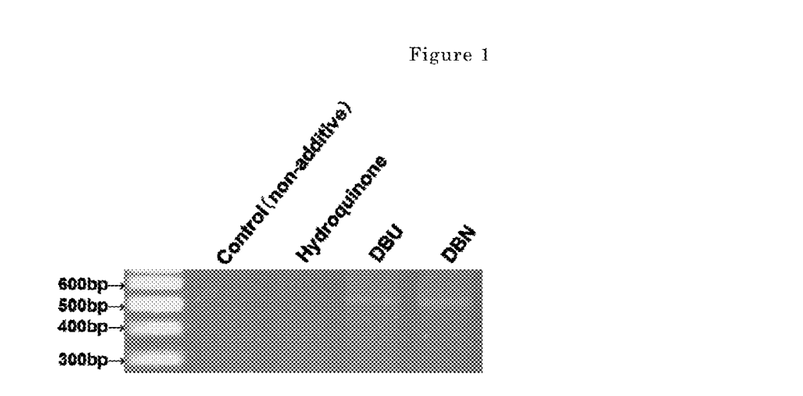
FIG. 1 shows the result of agarose gel electrophoresis carried out for the PCR amplification products obtained in Comparable Example 1 to 2 and Example 1 to 2.
Figure 2:
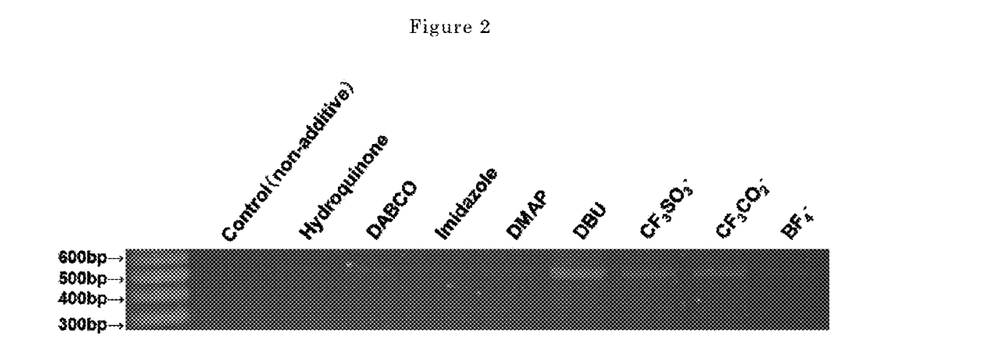
FIG. 2 shows the result of agarose gel electrophoresis carried out for the PCR amplification products obtained in Comparable Example 1 to 2, Example 1 and Example 3 to 8.
Figure 3:
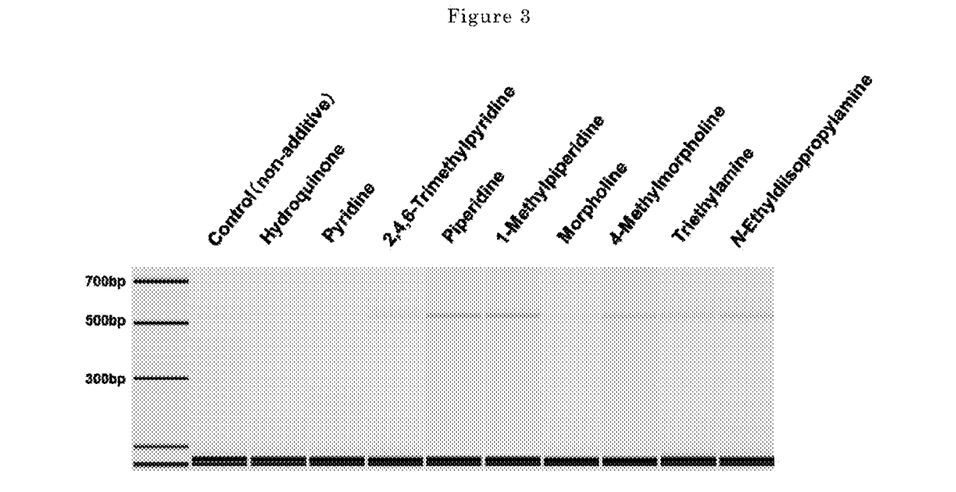
FIG. 3 shows the result of electrophoresis carried out by Agilent 2100 Bioanalyzer for the PCR amplification products obtained in Comparable Example 1 to 2, and Example 9 to 16.

The results are shown in FIG. 1 to 3. In addition, the confirmation results thereof are shown in Table 4. It should be noted that, as for the obtained amplified products, these were divided into 5 grades based on color density of their band (amount of amplified product), and the results are shown in Table 4. That is, the grade was represented by, in the order of the density, ⊚ (clear band), ○ (slightly faint band), Δ (faint band), ▲ (fairly faint band), and X represents the one which was not seen the band (the one which was not amplified).

TABLE 4

| Example | Name of compound | Confirmation of amplification |
|---|---|---|
| Example 1 | DBU | ⊚ |
| Example 2 | DBN | ⊚ |
| Example 3 | DABCO | ▲ |
| Example 4 | Imidazole | ▲ |
| Example 5 | DMAP | ▲ |
| Example 6 | Ionic liquid CF$_3$SO$_3$-type | ▲ |
| Example 7 | Ionic liquid CF$_3$CO$_2$-type | ▲ |
| Example 8 | Ionic liquid BF$_4$-type | ▲ |
| Example 9 | Pyridine | ▲ |
| Example 10 | 2,4,6-Trimethylpyridine | ▲ |
| Example 11 | Piperidine | ○ |
| Example 12 | 1-Methylpiperidine | ○ |
| Example 13 | Morpholine | ▲ |
| Example 14 | 4-Methylmorpholine | Δ |
| Example 15 | Triethylamine | Δ |
| Example 16 | N-Ethyldiisopropylamine | Δ |
| Comparative Example 1 | Absent | X |
| Comparative Example 2 | Hydroquinone | X |

As is clear from the above-described results, in the case of bisulfite reaction which was performed in the absence of additive substance (control), and the case where the bisulfite reaction with the addition of hydroquinone, which was conventional method, the PCR amplification product could not be confirmed.

On the other hand, when the bisulfite reaction was performed with the addition of various compounds of the above-described Examples, in any Examples, the amplification product could be confirmed at the position of objective chain length. In particular, when DBU and DBN were added, a large amount of amplification product could be confirmed; and in the case with piperidine and 1-methylpiperidine, the amplification product could also be confirmed clearly. As for the case where the other compounds in Examples were added, although the color density was low, the amplified product could be confirmed. From the results described above, in the bisulfite reaction performed with addition of compounds of the above-described Examples, it was anticipated that these compounds had a reaction promoting effect on the bisulfite reaction and a degradation suppressing effect on the genomic DNA.

Example 17

Cloning and Nucleotide Sequence Analysis of PCR Amplification Product

As for the PCR amplification product (DBU addition) obtained in Example 1 and the PCR amplification product (DBN addition) obtained in Example 2, cloning and nucleotide sequence analysis were carried out.

That is, to each 3 µL of the PCR amplification products obtained in Example 1 and Example 2, 1 µL of pGEM-T Easy Vector (produced by Promega Corporation) and 4 µL of DNA Ligation Kit (Takara Bio, Inc.) were added to make a total volume 8 µL, and incubated at 16° C. for 60 minutes.

To each 8 µL of solution containing the PCR amplification product inserted in a vector, 100 µL of E. coli (XL10 Gold, produced by Stratagene Corp.) was added, then incubation was carried out at 42° C. for 50 seconds by heat shock method. Subsequently, the transformed E. coli was cultured on an LB agar medium at 37° C. overnight. From a colony of cultured E. coli, a portion was extracted and dissolved in 5.9 µL of sterile water. To said sterile water, 1 µL of 10×Gene Taq Universal Buffer (produced by Nippon Gene Co., Ltd.), 1 µL of dNTPs mixed solution (each 2.5 mmol) (produced by Nippon Gene Co., Ltd.), 0. 1 µL of Gene Taq NT (produced by Nippon Gene Co., Ltd.), and each 1 µL of 2 kinds of primers having sequences derived from 5 µL of pGEM-T Easy Vector (produced by Promega Corporation) [5' CCAGTCACGACGTTGTAAAACG 3'(SEQ ID NO: 3) and 5' CACACAGGAAACAGCTATGACC 3' (SEQ ID NO: 4), designed so as to provide a chain length of insertion fragment +250 bp] were added respectively to make the total volume 10 µL, and by setting the reactions at 95° C. for 2 minutes, at 95° C. for 20 seconds, at 60° C. for 20 seconds, and at 72° C. for 30 seconds as 1 cycle, 30 cycles of colony PCR was performed. After that, the obtained each colony PCR amplification products were fractionated by electrophoresis using 1.5% agarose gel, and confirmed whether the colony was a vector-inserted one. Using the colony in which insertion of vector was confirmed, it was cultured with shaking in a LB medium at 37° C. overnight. Subsequently, using the obtained culture solution, and by using QuickGene Plasmid kit SII (produced by Fuji Film Co., Ltd.), the plasmid was extracted.

Figure 4:
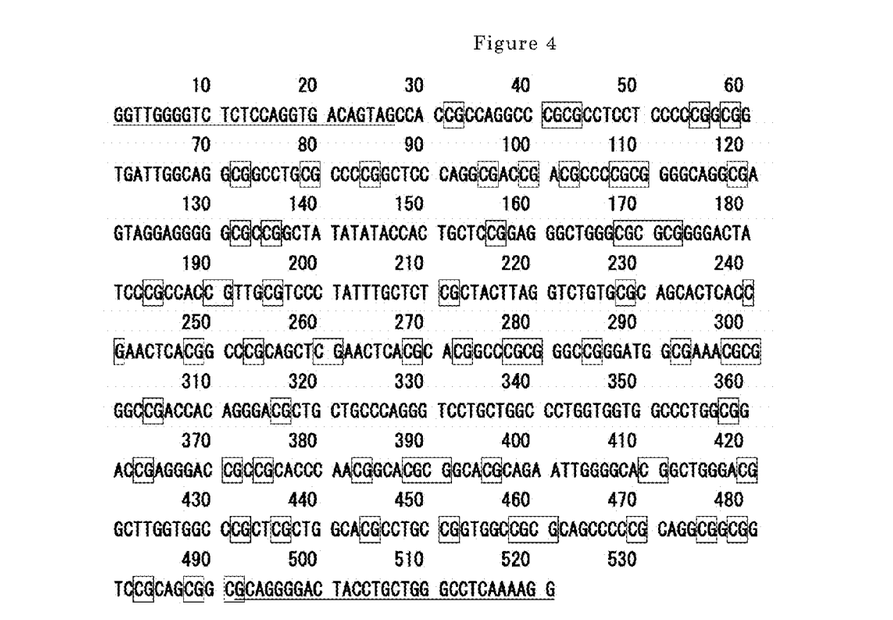
FIG. 4 shows the result of nucleotide sequence decoding of the PCR amplification product (method added with DBU) of Example 1 and the PCR amplification product (method added with DBN) of Example 2. The nucleotide sequence depicted in FIG. 4 is SEQ ID NO: 5.

As for the obtained 2 kinds of plasmid, decoding of nucleotide sequence was carried out by Applied Biosystems 3730×1 DNA Analyzer (Life Technologies Japan, Ltd.) using a sequence of the primer [5'CACACAGGAAACA-GCTATGACC 3' (SEQ ID NO: 4)] derived from pGEM-T Easy Vector (produced by Promega Corporation). The result of nucleotide sequence decoding of the PCR amplification product (by a method added with DBU) and the result of nucleotide sequence decoding of the PCR amplification product (by a method added with DBN) showed the same tendency. The results are shown in FIG. 4. In FIG. 4, the place framed by □ represents CpG dinucleotide, and underline indicates the primer part. In addition, the CpG dinucleotide was present in 61 places.

Figure 5:
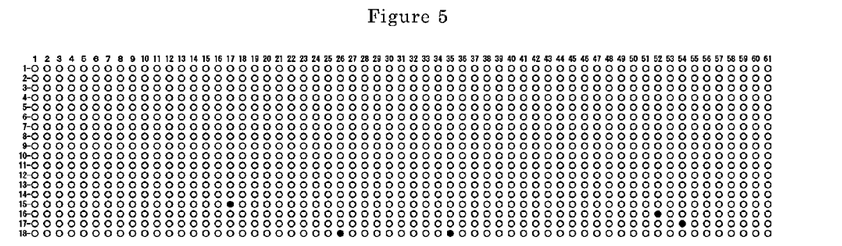
FIG. 5 is a map representing that the cytosine of CpG dinucleotide is either non-methylated cytosine or methylated cytosine for the PCR amplification products (by a method added with DBU) of Example 1.
Figure 6:
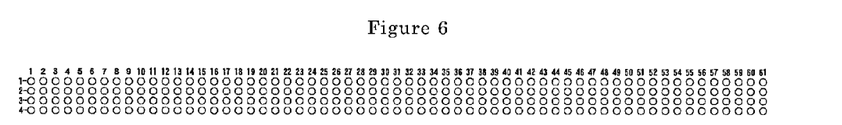
FIG. 6 is a map representing that the cytosine of CpG dinucleotide is either non-methylated cytosine or methylated cytosine, for the PCR amplification products (method added with DBN) of Example 2.

In addition, as for the decoding result of nucleotide sequence of the PCR amplification product (method of DBU addition) of Example 1, the figure illustrating whether the cytosine of the CpG dinucleotide is non methylated cytosine or methylated cytosine is shown in FIG. 5; as for the decoding result of nucleotide sequence of the PCR amplification product (method of DBN addition) obtained in Example 2, the figure illustrating whether the cytosine of the CpG dinucleotide is non methylated cytosine or methylated cytosine is shown in FIG. 6, respectively. It should be noted that, in FIG. 5 and FIG. 6, a mark ○ indicates that the CpG dinucleotide is the one derive from a non-methylated, and a mark ● indicates that the CpG dinucleotide is a methylated one.

In ES cell, since DNA in a promoter region of Fgf4, which is an undifferentiation marker of the stem cell, is not methylated, if said DNA is subjected to the uracilation reaction of the present invention, and all of these CpG dinucleotides are non-methyrated, it would be able to prove that the non-methylated cytosine has been converted into uracil with high efficiency. From the results of FIGS. 5 and 6, it turned out that the cytosine of almost all CpG dinucleotides and other cytosines have been converted into uracil. That is, it turned out that according to the method of the present invention, non-methylated cytosine can be converted into uracil with high efficiency.

DESCRIPTION OF REFERENCE NUMERALS

In FIG. 4, the place framed by □ represents CpG dinucleotide, and underline indicates the primer part. In FIG. 5 and FIG. 6, ○ indicates that the cytosine in the CpG dinucleotide is a non-methylated one, and ● indicates that the cytosine in the CpG dinucleotide is a methylated one.

What is claimed is:

1. A method for converting non-methylated cytosine in a single-stranded DNA to uracil, comprising subjecting the single-stranded DNA to a bisulfite reaction in the presence of at least one compound selected from the group consisting of:

a compound of formula [1]

[1]

wherein $R_1$ to $R_6$ represent each independently a hydrogen atom or an alkyl group having 1 to 3 carbon atoms; and n represents an integer of 1 to 3; and a compound of formula [2]

[2]

wherein Y represents a carbon atom; $R_7$ to $R_{12}$ represent each independently a hydrogen atom or an alkyl group having 1 to 3 carbon atoms; and k represents an integer of 2.

2. The method according to claim 1, wherein $R_1$ to $R_6$ are all hydrogen atoms.

3. The method according to claim 1, wherein $R_7$ to $R_{11}$ are all hydrogen atoms, $R_{12}$ is an alkyl group having 1 to 3 carbon atoms, and k is an integer of 2.

4. The method according to claim 1, comprising subjecting a single-stranded DNA to a bisulfite reaction in the presence of at least one compound of formula [1].

5. A method for amplifying single-stranded DNA in which non-methylated cytosine has been converted into uracil, comprising providing a single-stranded DNA in which non-methylated cytosine has been converted into uracil in accordance with the method of claim 1, and subjecting the single-stranded DNA in which non-methylated cytosine has been converted into uracil to a PCR reaction.

6. A method for detecting methylated cytosine in a single-stranded DNA, comprising proving an amplified single-stranded DNA in which non-methylated cytosine has been converted into uracil in accordance with claim 5, and subjecting the amplified single-stranded DNA to nucleotide sequence analysis to detect methylated cytosine therein.

7. The method according to claim 4, wherein $R_1$ to $R_6$ are all hydrogen atoms.

8. The method according to claim 1, comprising subjecting a single-stranded DNA to a bisulfite reaction in the presence of at least one compound of formula [2].

9. The method according to claim 8, wherein $R_7$ to $R_{11}$ are all hydrogen atoms, $R_{12}$ is an alkyl group having 1 to 3 carbon atoms, and k is an integer of 2.

10. A method for amplifying single-stranded DNA in which non-methylated cytosine has been converted into uracil, comprising providing a single-stranded DNA in which non-methylated cytosine has been converted into uracil in accordance with the method of claim 4, and subjecting the single-stranded DNA in which non-methylated cytosine has been converted into uracil to a PCR reaction.

11. A method for detecting methylated cytosine in a single-stranded DNA, comprising providing an amplified single-stranded DNA in which non-methylated cytosine has been converted into uracil in accordance with claim 10, and subjecting the amplified single-stranded DNA to nucleotide sequence analysis to detect methylated cytosine therein.

12. A method for amplifying single-stranded DNA in which non-methylated cytosine has been converted into uracil, comprising providing a single-stranded DNA in which non-methylated cytosine has been converted into uracil in accordance with the method of claim 7, and subjecting the single-stranded DNA in which non-methylated cytosine has been converted into uracil to a PCR reaction.

13. A method for detecting methylated cytosine in a single-stranded DNA, comprising providing an amplified single-stranded DNA in which non-methylated cytosine has been converted into uracil in accordance with claim 12, and subjecting the amplified single-stranded DNA to nucleotide sequence analysis to detect methylated cytosine therein.

14. A method for amplifying single-stranded DNA in which non-methylated cytosine has been converted into uracil, comprising providing a single-stranded DNA in which non-methylated cytosine has been converted into uracil in accordance with the method of claim 8, and subjecting the single-stranded DNA in which non-methylated cytosine has been converted into uracil to a PCR reaction.

15. A method for detecting methylated cytosine in a single-stranded DNA, comprising providing an amplified single-stranded DNA in which non-methylated cytosine has been converted into uracil in accordance with claim 14, and subjecting the amplified single-stranded DNA to nucleotide sequence analysis to detect methylated cytosine therein.

16. A method for amplifying single-stranded DNA in which non-methylated cytosine has been converted into uracil, comprising providing a single-stranded DNA in which non-methylated cytosine has been converted into uracil in accordance with the method of claim 9, and subjecting the single-stranded DNA in which non-methylated cytosine has been converted into uracil to a PCR reaction.

17. A method for detecting methylated cytosine in a single-stranded DNA, comprising providing an amplified single-stranded DNA in which non-methylated cytosine has been converted into uracil in accordance with claim 16, and subjecting the amplified single-stranded DNA to nucleotide sequence analysis to detect methylated cytosine therein.

* * * * *

SEQUENCE LISTING

```
<160> NUMBER OF SEQ ID NOS: 5

<210> SEQ ID NO 1
<211> LENGTH: 27
<212> TYPE: DNA
<213> ORGANISM: Artificial Sequence
<220> FEATURE:
<223> OTHER INFORMATION: Primer

<400> SEQUENCE: 1
ggttggggtt tttttaggtg atagtag                                       27
```

<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2 cctttaaaa cccaacaaat aatcccctac        30

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
ccagtcacga cgttgtaaaa cg        22

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
cacacaggaa acagctatga cc        22

<210> SEQ ID NO 5
<211> LENGTH: 521
<212> TYPE: DNA
<213> ORGANISM: Artificial Sequence
<220> FEATURE:
<223> OTHER INFORMATION: Synthetic Fgf4 promoter

<400> SEQUENCE: 5
ggttggggtc tctccaggtg acagtagcca ccgccaggcc cgcgcctcct ccccccggcgg        60 tgattggcag gcggcctgcg ccccggctcc caggcgaccg acgccccgcg gggcaggcga       120
gtaggagggg gcgccggcta tatataccac tgctccggag ggctgggcgc gcggggacta       180
tcccgccacc gttgcgtccc tatttgctct cgctacttag gtctgtgcgc agcactcacc       240
gaactcacgg cccgcagctc gaactcacgc acggcccgcg ggccgggatg gcgaaacgcg       300
ggccgaccac agggacgctg ctgcccaggg tcctgctggc cctggtggtg gccctggcgg       360
accgagggac cgccgcaccc aacggcacgc ggcacgcaga attggggcac ggctgggacg       420
gcttggtggc ccgctcgctg gcacgcctgc cggtggccgc gcagccccg caggcggcgg       480 tccgcagcgg cgcaggggac tacctgctgg gcctcaaaag g       521

UNITED STATES PATENT AND TRADEMARK OFFICE
CERTIFICATE OF CORRECTION

PATENT NO. : 9,624,535 B2  
APPLICATION NO. : 14/364545  
DATED : April 18, 2017  
INVENTOR(S) : Hayashida et al.

Page 1 of 1

It is certified that error appears in the above-identified patent and that said Letters Patent is hereby corrected as shown below:

In the Claims

Claim 6, Column 29, Line 56, "proving" should read "providing"

Signed and Sealed this  
Twenty-ninth Day of August, 2017

Joseph Matal  
*Performing the Functions and Duties of the*  
*Under Secretary of Commerce for Intellectual Property and*  
*Director of the United States Patent and Trademark Office*